United States Patent [19]

Graber et al.

[11] Patent Number: 4,602,945
[45] Date of Patent: Jul. 29, 1986

[54] ACARICIDAL ESTER OF TRICYCLOHEXYL-TIN HYDROXIDE

[75] Inventors: Geràrd Graber, Lyon; Bernard Marcoux, Saint Etienne, both of France

[73] Assignee: Rhone-Poulenc Agrochimie, Lyon, France

[21] Appl. No.: 592,353

[22] Filed: Mar. 22, 1984

[30] Foreign Application Priority Data

Mar. 22, 1983 [FR] France ................................ 83 04884

[51] Int. Cl.$^4$ .......................... C07F 7/22; A01N 55/02
[52] U.S. Cl. ......................................... 71/97; 556/94; 514/493
[58] Field of Search ........................ 260/429.7; 556/94

[56] References Cited

U.S. PATENT DOCUMENTS

| | | |
|---|---|---|
| 3,083,217 | 3/1963 | Sawyer et al. ................ 260/429.7 X |
| 3,097,999 | 7/1963 | Koopmans ................... 260/429.7 X |
| 3,129,236 | 4/1964 | Weissenberger ................ 260/429.7 |
| 3,264,177 | 8/1966 | Kenega ........................ 260/429.7 X |
| 3,400,201 | 9/1968 | Mocotte ....................... 260/429.7 X |
| 3,542,824 | 11/1970 | Bublitz ............................. 260/429.7 |
| 3,598,849 | 8/1971 | Bublitz ............................. 260/429.7 |
| 3,703,588 | 11/1972 | Saito et al. ................... 260/429.7 X |
| 3,790,611 | 2/1974 | Gitlitz et al. ...................... 260/429.7 |
| 3,861,949 | 1/1975 | Onozuka et al. ............. 260/429.7 X |
| 4,224,338 | 9/1980 | Sbragia et al. ............... 260/429.7 X |

OTHER PUBLICATIONS

Chemical Reviews, vol. 60, pp. 494 and 498–501 (1960).
Luijten et al, Investigations in the Field of Organotin Chem.; Tin Res. Inst., England, pp. 92–95, 98, 99, 104, 105, 107, 109, 111, 112 (1955).
Poller, The Chemistry of Organotin Compounds, Acad. Press, N.Y., pp. 173 & 177 (1970).

*Primary Examiner*—Helen M. S. Sneed
*Attorney, Agent, or Firm*—Burns, Doane, Swecker & Mathis

[57] ABSTRACT

Tricyclohexyl-tin benzoate and insectidical and/or acaricidal compositions comprising an insecticidally and/or acaricidally effective amount of tricyclohexyl-tin benzoate. Tricyclohexyl-tin benzoate has an excellent acaricidal activity and a remarkable solubility in the usual solvents used in agrochemistry. Because of the high solubility, tricyclohexyl-tin benzoate can be easily formulated in the form of an emulsifiable concentrate.

5 Claims, No Drawings

ACARICIDAL ESTER OF TRICYCLOHEXYL-TIN HYDROXIDE

The present invention relates to a new organic derivative of tin, a method for its preparation, insecticidal and acaricidal compositions containing this derivative and a method of treating plants with these compositions to protect them from phytophagous insects and acarids.

Tricyclohexyl-tin hydroxide, better known by its common name cyhexatin, is a known acaricide which is noteworthy for its specific activity against phytophagous acarids, in particular in arboriculture and in the cultivation of vegetables and ornamental plants. This product is used in the form of a wettable powder and, more recently, an emulsifiable concentrate. However, this latter formulation is difficult to obtain because of the insolubility of cyhexatin in most of the usual solvents in agrochemistry. Complicated emulsifier systems which do not ensure that the formulation has a genuinely satisfactory stability have thus had to be used.

The Applicant Company has now discovered a new active ingredient consisting of an organic derivative of tin, which also has an excellent acaricidal activity and moreover, surprisingly, can very easily be formulated in the form of an emulsifiable concentrate because of its remarkable solubility in the usual solvents in agrochemistry.

The invention thus relates to a new organic derivative of tin, consisting of tricyclohexyl-tin benzoate. It also relates to acaricidal compositions containing this product as the active ingredient, and in particular emulsifiable concentrates, which can be used to treat plants against phytophagous acarids.

Tricyclohexyl-tin benzoate is a compound of the formula:

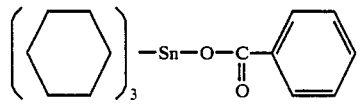

It can be prepared, for example, by the action of benzoic acid on tricyclohexyl-tin hydroxide. This reaction is carried out in an organic solvent medium, such as toluene, xylene, chlorobenzene, polychlorobenzene or cyclohexanone, at a temperature of, in general, at most 60°. The water formed in the course of the reaction is preferably removed at the rate at which it is formed, for example by absorption with a water-soluble salt, such as sodium sulphate or magnesium sulphate, or by azeotropic distillation of the solvent/water mixture. The isolated product obtained is in the form of a white crystalline powder of melting point 111° C.

The following examples illustrate on the one hand the preparation and physicochemical properties of the compound according to the invention, in particular its excellent solubility in most of the organic solvents, and on the other hand its excellent acaricidal properties.

EXAMPLE 1

A 20 liter reactor is charged with tricyclohexyltin hydroxide (2,326 g, 6.04 mol), anhydrous toluene (9 liters) and benzoic acid (737 g, 6.04 mol). The mixture is heated at about 50°–60° C., with stirring, for 1 hour 30 minutes and cooled to room temperature. Anhydrous sodium sulphate (1,500 g) is then added and stirring is continued for 1 hour. The mixture is filtered and the filtrate is concentrated under reduced pressure (6 mm Hg=789 Pa) at 50° C. A white solid product precipitates and is recrystallised from hexane (3,250 ml) at 50° C. The product precipitates by cooling to 10°–15° C. It is dried and rinsed with cold hexane (750 ml). After drying in a drying oven at 30° C. under reduced pressure (6 mm Hg=789 Pa), tricyclohexyl-tin benzoate (2,185 g) is thus obtained. The hexane filtrate is concentrated and a second portion of product (362 g) is obtained.

| Total weight obtained: | 2,547 g |
|---|---|
| Yield: | 86.8% |
| Melting point: | 111° C. |

The structure shown is confirmed by analysis by infrared and proton NMR spectrometry.

EXAMPLE 2

An emulsifiable concentrate having the following composition, for one liter of formulation, is prepared:

| | |
|---|---|
| tricyclohexyl-tin benzoate | 411 g |
| calcium dodecylbenzenesulphonate in 60% strength solution in isopropanol | 50 g |
| a 30–33:1 ethylene oxide/castor oil condensate | 50 g |
| xylene | 498 g | specific gravity at 20° C.: 1.008

EXAMPLE 3

A reactor is charged, with cyclohexanone (546 g) and 94% pure tricyclohexyl-tin hydroxide (316 g) at 50° C., with stirring. The tin derivative does not dissolve. Benzoic acid (95 g) is then added and the temperature is kept at 50° C. After stirring for 10 minutes, a yellow solution is obtained which, after filtration and drying, gives a clear solution. An emulsifiable concentrate of specific gravity 1.057 at 20° C. is obtained by adding emulsifiers as in the preceding example.

EXAMPLE 4

If the procedure in the preceding example is followed, the same results are obtained, starting from the following mixture:

| | |
|---|---|
| tricyclohexyl-tin benzoate | 411 g |
| acetophenone | 285 g |
| xylene | 279 g |
| calcium dodecylbenzenesulphonate in 60% strength solution in isopropanol | 50 g |
| a 30–33:1 ethylene oxide/castor oil condensate | 50 g |

An emulsifiable concentrate of specific gravity 1.075 at 20° C. is obtained.

EXAMPLE 5

Acaricidal tests

Bean plants at the stage of 1 trifoliate leaf are contaminated with a mixed population of *Tetranychus urticae*.

After 48 hours, the contaminated plants are treated with aqueous dilutions of the compositions to be tested, using a spray gun of the FISCHER type, until dripping wet. These compositions consist of:

(a) for reference, a commercial composition PLIC-TRAN 600 F, i.e. a concentrated aqueous suspension of 600 g/liter of cyhexatin, and (b) the emulsifiable concentrate according to the invention obtained in Example 3.

Three bean plants are used per product and per dose. The treated plants are kept in a greenhouse for 14 days (temperature 20°-25° C., relative humidity 40-60%, illumination 5 to 10,000 lux). The plants are watered at the foot, to avoid any washing off of the products.

After 2, 7 and 14 days after the treatment, the population of acarids present on each plant is estimated in relation to the mean of 3 controls treated only with water. A percentage activity is deduced therefrom:

$$\text{Example: } 100\% - \frac{\text{Population on the treated plant}}{\text{Population on the untreated plant}} \text{ in } \%$$

Under these conditions, the results shown in the following table are found:

| Product | Active ingredient in g/hl | % activity at n days | | |
|---|---|---|---|---|
| | | 2 | 7 | 14 |
| Reference | 30 | 90 | 100 | 100 |
| | 15 | 70 | 90 | 100 |
| | 5 | 50 | 90 | 90 |
| Invention | 30 | 80 | 100 | 100 |
| | 15 | 80 | 100 | 100 |
| | 5 | 50 | 80 | 80 |
| Control | 0 | 0 | 0 | 0 |

Furthermore, no phytotoxicity was found.

If the test is carried out in the same manner on another species of acarids, Polyphagotarsonemus, it is found that the lethal dose at 90%, in ppm, is 10 for tricyclohexyl-tin benzoate, i.e. eight times less than that for the reference cyhexatin (used as a wettable powder).

EXAMPLE 6

Insecticidal test

Discs of leaf from turnip plants are placed in gelose in Petri dishes. In each dish, 10 *Plutella xylistella* larvae are placed on each disc and the dish is covered with a ventilated lid. The product to be tested is dissolved in a water/acetone 50/50 mixture and the discs are treated by spraying with this solution by using a Potter tower at a dose equivalent to 675 liters/ha. The discs are kept at 26° C. After 48 hours after the treatment, the live and dead larvae are counted and the mortality percentage is calculated.

Under these conditions, it is found that tricyclohexyl-tin benzoate causes a mortality of at least 95% at a dose of 100 g/hl, whilst cyhexatin, taken as a reference in the form of a wettable powder, is virtually inactive (<10%) at the same dose.

These examples clearly show:

the remarkable solubility of the compound according to the invention which enables it to be easily introduced into formulations of the emulsifiable concentrate type and enables it to be combined with other active ingredients of agrochemistry, the excellent acaricidal activity of the compound according to the invention, which is more multivalent than the reference, and a complementary insecticidal activity which the reference does not possess.

This compound can thus be used to combat insects, and more particularly phytophagous acarids, in crops such as, in particular, vineyards, arboriculture, vegetable crops and ornamental plants.

It is advantageously applied in doses of 0.05 to 5 kg/ha, preferably 0.1 to 2 kg/ha.

For its use in practice, the compound according to the invention is rarely employed by itself. Most frequently, it is used in compositions. These compositions, which can be used to protect plants from fungicidal diseases, contain, as the active ingredient, the compound according to the invention as described above in combination with solid or liquid carriers which are acceptable in agriculture and surface-active agents which are also acceptable in agriculture. In particular, the usual inert carriers and the usual surface-active agents can be used.

These compositions can also contain any other type of ingredient, such as, for example, protective colloids, adhesives, thickeners, thixotropic agents, penetration agents, stabilisers, sequestering agents and the like, as well as other known active ingredients with pesticidal properties (in particular insecticides or fungicides) or with plant growth-promoting properties (in particular fertilisers) or with plant growth-regulating properties. More generally, the compounds according to the invention can be combined with all solid or liquid additives in accordance with the conventional techniques of formulation.

In general, compositions containing 0.5 to 5,000 ppm of active substance are very suitable; these values are given for ready-to-use compositions. "ppm" means "parts per million". The range from 0.5 to 5,000 ppm corresponds to a range of from $5 \times 10^{-5}\%$ to 0.5% (percentages by weight).

As regards compositions suitable for storage and transportation, these more advantageously contain 0.5 to 95% (by weight) of active substance.

The compositions to be used in agriculture according to the invention can thus contain the active ingredients according to the invention within very wide limits, i.e. of from $5.10^{-5}\%$ to 95% (by weight).

In accordance with the above statements, the compounds according to the invention are generally combined with carriers and, if appropriate, surface-active agents.

In the present account, the term "carrier" denotes an organic or inorganic, natural or synthetic material with which the active ingredient is combined in order to facilitate its application to the plant, to seeds or to the soil. This carrier is therefore generally inert and it must be acceptable in agriculture, in particular on the plant treated. The carrier can be solid (clays, natural or synthetic silicates, silica, resins, waxes, solid fertilisers and the like) or liquid (water, alcohols, ketones, petroleum fractions, aromatic or paraffinic hydrocarbons, chlorohydrocarbons, liquefied gases and the like).

The surface-active agent can be an emulsifying, dispersing or wetting agent of the ionic or non-ionic type. Examples which may be mentioned are polyacrylic acid salts, lignosulphonic acid salts, phenylsulphonic or naphthalenesulphonic acid salts, polycondensates of ethylene oxide with fatty alcohols, fatty acids or fatty amines, substituted phenols (in particular alkylphenols or arylphenols), salts of sulphosuccinic acid esters, taurine derivatives (in particular alkyltaurates) and phosphoric acid esters of polycondensates of ethylene oxide with alcohols or phenols. The presence of at least one surface-active agent is generally essential, if the active ingredient and/or the inert carrier are not soluble in water and if the vehicle of application is water.

For its application, the compound of the invention is thus generally in the form of compositions; these compositions according to the invention are themselves in a fairly wide variety of solid or liquid forms.

As forms of solid compositions, there may be mentioned powders for dusting or dispersion (with a content of compound of the formula (I) which can range up to 100%) and granules, in particular those obtained by extrusion, by compacting, by impregnation on a granular carrier or by granulation of a powder (the content of compound of the formula (I) in these granules is between 1 and 80% in the latter cases).

As forms of liquid compositions or compositions which are to be made up into liquid compositions on application, there may be mentioned solutions, in particular emulsifiable concentrates, ultra-low volume (or ULV) formulations, emulsions, suspension concentrates, aerosols, wettable powders (or spraying powder) and pastes.

The emulsifiable concentrates most frequently comprise 10 to 80% of active ingredient, and the ready-to-use emulsions or solutions contain 0.01 to 20% of active ingredient. In addition to the solvent, the emulsifiable concentrates may contain, where necessary, 2 to 20% of suitable additives, such as stabilisers, surface-active agents, penetrating agents, corrosion inhibitors, dyestuffs and adhesives. The following is an example of the composition of some concentrates:

| active ingredient | 400 g/liter |
|---|---|
| alkali metal dodecylbenzenesulphonate | 24 g/liter |
| 10:1 ethylene oxide/nonylphenol condensate | 16 g/liter |
| cyclohexanone | 200 g/liter |
| aromatic solvent q.s.p. | 1 liter |

The following are used in another formulation of an emulsifiable concentrate:

| active ingredient | 250 g |
|---|---|
| expoxidised vegetable oil | 25 g |
| mixture of alkylaryl sulphonate and a polyglycol/fatty alcohol ether | 100 g |
| dimethylformamide | 50 g |
| xylene | 575 g |

The following are used in another formulation of an emulsifiable concentrate:

| active ingredient | 450 g |
|---|---|
| condensate of ethylene oxide with tristyrylphenol | 50 g |
| alkali metal dodecylbenzenesulphonate | 50 g |
| chlorobenzene q.s.p. | 1 liter |

From these concentrates, emulsions of any desired concentration can be obtained by dilution with water, these being particularly suitable for application to the leaves.

For application called "ultra-low volume" (U.L.V.) with a spray of very fine droplets, solutions in organic solvents containing 70 to 99% of active ingredient are prepared.

An ultra-low volume formulation is prepared, for example, with the following composition:

| active ingredient | 200 g |
|---|---|
| paraffinic/aromatic oil | 200 g |
| aromatic solvent q.s.p. | 1 liter |

The following is another ultra-low volume formulation:

| tricyclohexyl-tin benzoate | 150 g |
|---|---|
| cypermethrin | 30 g |
| triazophos | 125 g |
| paraffinic/aromatic oil | 150 g |
| betapinene | 19 g |
| acetic anhydride | 15 g |
| cyclohexanone q.s.p. | 1 liter |

The suspension concentrates, which can also be applied by spraying are prepared so as to give a stable fluid product which does not form a deposit, and they usually contain from 10 to 75% of active ingredient, from 0.5 to 15% of surface-active agents, from 0.1 to 10% of thixotropic agents, from 0 to 10% of suitable additives, such as anti-foam agents, corrosion inhibitors, stabilisers, penetrating agents and adhesives, and, as the carrier, water or an organic liquid in which the active ingredient is sparingly soluble or insoluble: certain solid organic substances or inorganic salts can be dissolved in the carrier in order to assist in preventing sedimentation or to act as anti-freeze agents for the water.

The wettable powders (or spraying powder) are usually prepared so as to contain 20 to 95% of active ingredient, and they usually contain, in addition to the solid carrier, from 0 to 5% of a wetting agent, from 3 to 10% of a dispersing agent and, where necessary, from 0 to 10% of one or more stabilisers and/or other additives, such as penetrating agents, adhesives, anti-caking agents, dyestuffs and the like.

The following are examples of various compositions of wettable powders:

| active ingredient | 50% |
|---|---|
| calcium lignosulphonate (deflocculant) | 5% |
| isopropyl naphthalenesulphonate (anionic wetting agent) | 1% |
| anticaking silica | 5% |
| kaolin (filler) | 39% |
| 70% strength wettable powder: | |
| active ingredient | 700 g |
| sodium dibutylnaphthylsulphonate | 50 g |
| 3:2:1 condensation product of naphthalene-sulphonic acid, phenylsulphonic acid and formaldehyde | 30 g |
| kaolin | 100 g |
| champagne chalk | 120 g |
| 40% strength wettable powder: | |
| active ingredient | 400 g |
| sodium lignosulphonate | 50 g |
| sodium dibutylnaphthalene sulphonate | 10 g |
| silica | 540 g |
| 25% strength wettable powder: | |
| active ingredient | 250 g |
| calcium lignosulphonate | 45 g |
| mixture of equal parts by weight of champagne chalk and hydroxyethylcellulose | 19 g |
| sodium dibutylnaphthalene sulphonate | 15 g |
| silica | 195 g |
| champagne chalk | 195 g |
| kaolin | 281 g |
| 25% strength wettable powder: | |

| -continued | |
| --- | --- |
| active ingredient | 250 g |
| isooctylphenoxy-polyoxyethylene-ethanol | 25 g |
| mixture of equal parts by weight of champagne chalk and hydroxyethylcellulose | 17 g |
| sodium aluminosilicate | 543 g |
| kieselguhr | 165 g |
| 10% strength wettable powder: | |
| active ingredient | 100 g |
| mixture of sodium salts of saturated fatty acid sulphates | 30 g |
| condensation product of naphthalene-sulphonic acid and formaldehyde | 50 g |
| kaolin | 820 g |

To obtain these wettable powders, the active ingredient is intimately mixed with the additional substances in suitable mixers and the mixture is ground in mills or other suitable grinders. This gives powders of advantageous wettability and suspendability; they can be suspended in water at any desired concentration and this suspension can be used very advantageously, in particular for application to the leaves of the plants.

As already stated, the aqueous dispersions and aqueous emulsions, e.g. compositions obtained by diluting, with water, a wettable powder or an emulsifiable concentrate according to the invention, are included within the general scope of the present invention. The emulsions can be of the water-in-oil or oil-in-water type and they can have a thick consistency such as that of a "mayonnaise".

The granules, which are intended to be placed on the soil, are usually prepared so as to have dimensions of between 0.1 and 2 mm, and they can be manufactured by agglomeration or impregnation. In general, the granules contain 0.5 to 25% of active ingredient and 0 to 10% of additives, such as stabilisers, slow release modifiers, binders and solvents.

The compounds of the formula (I) can also be used in the form of dusting powders; it is also possible to use a composition containing 50 g of active ingredient and 950 g of talc; it is also possible to use a composition containing 20 g of active ingredient, 10 g of finely divided silica and 970 g of talc; these constituents are mixed and ground and the mixture is applied by dusting.

We claim:
1. The compound tricyclohexyl-tin benzoate.
2. An insecticidal and/or acaricidal composition which comprises an insecticidally and/or acaricidally effective amount of the compound according to claim 1.
3. A composition according to claim 2, which comprises an additional insecticidally effective amount of an insecticide.
4. A composition according to claim 2, which is an emulsifiable concentrate.
5. A method of treating plants against phytophagous insects and acarids, which comprises applying to said plants an insecticidally or acaricidally effective amount of the composition according to any one of claims 2 to 4.

* * * * *